United States Patent [19]

Harte et al.

[11] Patent Number: 4,540,660

[45] Date of Patent: Sep. 10, 1985

[54] SUBSTRATE FOR FLUOROIMMUNOASSAY OF BIOLOGICAL FLUIDS

[75] Inventors: Richard A. Harte, Redwood City; Anthony B. Chen, Hayward; Nancy K. Kaufman, Belmont, all of Calif.

[73] Assignee: Daryl Laboratories, Inc., Santa Clara, Calif.

[21] Appl. No.: 483,055

[22] Filed: Apr. 7, 1983

[51] Int. Cl.³ .............................................. G01N 33/54
[52] U.S. Cl. ....................................... 435/7; 436/518; 436/528; 436/531; 436/535
[58] Field of Search .................. 435/7; 436/518, 528, 436/531, 533, 535, 537

[56] References Cited

U.S. PATENT DOCUMENTS

| 4,340,564 | 7/1982 | Harte et al. | 435/7 |
| 4,363,634 | 12/1982 | Schall | 435/7 |
| 4,468,371 | 8/1984 | Chen et al. | 422/102 |

OTHER PUBLICATIONS

Journal of Applied Physics, vol. 52, (10), pp. 6197–6202, Popovic, Z. D.

*Primary Examiner*—David M. Naff
*Assistant Examiner*—Stephen C. Wieder
*Attorney, Agent, or Firm*—Felfe & Lynch

[57] ABSTRACT

A substrate for fluoroimmunoassay is disclosed comprising a swellable, rehydratable polymeric protein-binding material forming a three-dimensional matrix; first particulate, light scattering centers distributed in the polymeric matrix capable of scattering visible light; and second particulate, light-scattering centers distributed in the polymeric matrix capable of reflecting fluorescent excitation light and absorbing all other light. The substrate efficiently binds proteins and enhances transmitted fluorescent light and thus increases the sensitivity of assays involving fluorescent measurements. The polymeric protein binding material is preferable an acrylic copolymer. The first light scattering centers are preferably oxides of titanium and zinc, and the second light-scattering centers are preferably a phthalocyanin compound.

15 Claims, No Drawings

SUBSTRATE FOR FLUOROIMMUNOASSAY OF BIOLOGICAL FLUIDS

BACKGROUND

This invention relates to the fluoroassay of biological fluids. More particularly this invention relates to a substrate for fluoroimmunoassay which is capable of binding specific proteins and other biological entities (e.g. DNA). The substrate enhances the specificity and sensitivity of fluoroimmunoassay (FIA) and is thus useful in the diagnosis of diseases associated with specific antigens and antibodies. The invention is valuable in veterinary assays for diseases affecting companion, laboratory, and livestock animals as well as diseases and disease states in humans.

Fluoroassay is a powerful technique for detecting small amounts of substances in a complex mixture. It is especially useful in fluoroimmunoassay (FIA) of body fluids such as blood where small amounts of an antigen and antibodies which recognize it must be detected.

FIA is useful in diagnosis of a disease when it is specific for a particular antigen or antibody which is characteristic of that disease. However, for a reliable diagnosis, FIA must also be not only specific but also highly sensitive since the substance to be detected is often present in very small amounts in the fluid being analyzed.

Prior attempts to enhance the sensitivity of FIA include the development or use of substrates which selectively bind proteins. These substrates may be immobilized on solid surfaces so that the immunoreaction between antigen and antibody may be more easily observed.

However, these substrates have generally been comprised of polymers such as polystyrene or polypropylene which do not strongly bind proteins and thus are of limited use in selecting minute amounts of proteinaceous immunogens from complex biological fluids. A useful diagnostic assay requires a substrate which can efficiently adsorb particular antibodies or antigens.

Since FIA involves the detection of light emitted by a particular fluorophor, sensitivity also depends upon the intensity of light so emitted and its relation to background or scattered light. Choosing an incident wavelength to match excitation frequency of fluorophor is one important factor in increasing sensitivity. Harte et al. in U.S. Pat. No. 4,340,564 disclose a solid-phase immunosubstrate which comprises an over-coating of polymer beads with light scattering centers and binders which enhance scattered light. Other ways to improve substrates and increase the amount of transmitted light have been actively sought, e.g., see Pierce et al, U.S. Pat. No. 4,258,001, Mar. 24, 1981.

SUMMARY

The present invention provides a substrate for fluoroimmunoassay comprised of a swellable polymeric protein-binding, gel-like material which forms a three-dimensional, colloidal framework and light scattering centers randomly distributed therein.

More specifically, the present invention provides a substrate for fluorimmunoassay comprising a swellable poylmeric protein binding material forming a three-dimensional matrix; non-specific particulate light-scattering centers distributed in the polymeric matrix capable of scattering visible light; and specific particulate light-scattering centers distributed in the polymeric matrix capable of reflecting specific narrow band fluorescent excitation light and absorbing non-specific light.

Unlike most solid substrates, the substrate of the invention is a 3-dimensional matrix, a swellable, rehydratable film with colloidal, gel-like properties capable of binding 5 to 20 times as much protein as a comparable sized area of, for example, polystyrene. Characteristic of this film is its ability, when exposed to aqueous materials, to imbibe the liquid rapidly, swelling during the process of rehydration and thus permitting proteins to traverse within the film so that, for example, specific antibodies can reach and bind with their complementary antigens or vise versa, enzymes can reach their specific substrates.

The particulate, non-specific light scattering centers of the substrate enhance the sensitivity of fluoroimmunoassay with the substrate of the present invention by scattering both incident visible light and also emitted fluorescent light.

In the optical scheme of fluoroimmunoassay where the antigen or antibody introduced as the second reactant carried into the film, has bound to it a fluorescing dye molecule as an identifying label, said dye molecule is excited with wavelengths of light matching the light absorbing spectrum of the dye. When the dye molecule absorbs a photon of light within its specific excitation spectrum, an electron is raised to a higher energy state, and then through triplet state conversion, a photon of lesser energy (longer wavelength) is re-emitted. A specific scatterer of light associated with the fluorescence, would enhance transfer of such light to a detector. However, such particles would also absorb and, therefore, extinguish the original exciting light thus preventing excitation of the dye. Therefore, the non specific light scatterers of the present invention have been chosen to be nonspecific so as not to absorb the exciting light and still be able to scatter the emitted fluorescence light from the dye.

The specific, light scattering centers of the substrate scatter only the narrow band of light corresponding to the fluorescent excitation wavelengths of the dye. These specific light scatterers are pigments whose light scattering spectrum matches the light absorbing spectrum of the fluorescent dye. Transfer of incident light having wavelengths within this spectral range which excite the fluorescent label is thus enhanced. At sometime or other, interfering background light of different wavelength is absorbed and thus extinguished by these specific light scatterers. Since the transfer of fluorescent light is enhanced while background light is reduced by these specific light scatterers, the sensitivity of FIA with the substrate of the present invention is improved.

Therefore, the substrate of the present invention efficiently binds proteins and enhances transmitted fluorescent light and thus increases the sensitivity of assays involving fluorescent measurements.

DESCRIPTION

Preferably, the protein binding polymeric material of the present invention is a 3-dimensional, polymeric matrix which is a water swellable and rehydratable film having gel-like, colloidal properties, an acrylic copolymer, for example, preferably a water-based emulsion of acrylic copolymer resin. Embedded in the colloid film are light scattering centers of two types: (1) non-specific and (2) specific light scatterers.

Each is submicron in size and insoluble in aqueous media. The non-specific light scattering particulate centers are most preferably particles of zinc oxide or titanium dioxide (in its rutile form) either separate or combined. The non-specific light scattering particles may be non-organic, such as the anatase or rutile forms of titanium dioxide, zinc oxide, calcium carbonate; or they may be of clay origin, such as kaolin (china clay), bentonite or Fullers earth; or they may be of organic origin, such as starches. These light scatterers are particulate, are uniformly distributed, scatter all light efficiently and increase the probability of an exciting light photon reaching a fluorophor after reflections, if not in its original path.

The specific light scattering centers are also particulate, randomly distributed in the protein-binding polymeric latex and are most preferably a pigmented compound with specific desirable spectral reflectance. Most preferred is a metallic phthalocyanine salt, copper phthalocyanine, for example. The phthalocyanine compound (sometimes referred to herein as the "pigment") is a specific absorber of light whose spectral scattering distribution is matched to the excitation spectrum of the fluorescent dye employed and thus reduces any light of undesirable wavelength whether due to autofluorescence or background scatter. Thus, when one employs fluorescein isothiocyanate (FITC) as the dye whose spectral absorbance peaks in the "blue" portion of the spectrum at 470 nanometers, one would employ the particles of copper phthalocyanine whose spectral reflectance or scatter has been shown to be optimum at 470 nanometers. Should the dye employed be a rhodamine derivative which absorbs in the "green" region of the spectrum and fluoresces in the "orange" region of the spectrum, one should use the appropriate pigment to maximize scattering at about 530 nanometers wavelength. In cases where a nonfluorescent optical effect is being determined and both excitation and emission are identical, as in photometric changes employed in enzyme labelling techniques, no specific spectral scattering particle need be added to the emulsion which will form the colloid film.

It is preferred to use non-specific light scattering centers in a weight ratio of about thirty to one with respect to the specific light scattering centers.

In preferred embodiments of the present invention, the immunoadsorptive substrate is found in combination with a solid support. Most preferably, the solid support comprises an essentially flat surface as, for example, that of a test slide. Most preferably, however, the immunoadsorptive substrate is found as a relatively thick layer (40 to 50 microns in depth) on the essentially flat bottom of test wells in the solid support. The test wells are preferably of circular dimension with acutely sloping walls as disclosed, for example, in co-pending U.S. patent application Ser. No. 399,855 filed July 19, 1982, which is incorporated herein by reference.

The immunoadsorptive substrate of the present invention may additionally comprise an immunogenic reagent—either antigen or antibody. The substrate in these embodiments is especially useful in the analysis of blood or other body fluids for immunogenic reagents characteristic of a disease, especially those caused by viral, bacterial or parasitic infection.

The substrate is of use in diagnosis by immunogenic assay of biological fluids of small companion, live stock, and laboratory animals for such common viral, parasitic, and bacterial diseases by immunogenic assay of biological fluids for feline leukemia virus, feline infectious peritonitis, toxoplasmosis, feline infectious anemia, heartworm, canine brucellosis, canine parvovirus, antinuclear antibodies, rheumatoid factor, and canine distemper; diagnosis of equine animals for equine infectious anemia, equine pregnancy, equine strangles, equine pneumonitis, equine metritis and equine influenza; viral panels for laboratory mice and rats; bovine brucellosis; avian disorders including Newcastles disease virus, psittacosis and leukosis, diseases of swine such as trichinosis, gastroenteritis, pseudorabies and African swine fever.

Assays for toxoplasmosis suitable for use with the substrate of the present invention are described in:

Sabin, A. B., Feldman, H. A., Dyes as Microchemical Indicators of a New Immunity Phenomenon Affecting Protozoan Parasite (Toxoplasma) Science, 108 660–663 1948.

Jacobs, L., Lunde, M. N., A Hemagglutination Test for Toxoplasmosis J. Parasitol, 43 308–314 1957.

Sulzer, A. J., Hall, E. C., Indirect Fluorescent Antibody Tests for Parasitic Diseases IV, Statistical Study of Variation in the Indirect Fluorescent Antibody (IFA) for Toxoplasmosis Am. J. Epidemio, 86 401–407 1967.

Voller, A. D., Bidwell, G. Huldt, E. Engvall A. Microplate Method of Enzyme Linked Immunoassay for Toxoplasma Antibody J. Clin. Pathol. 29 150–153 1974.

Assays for feline infections peritonitis suitable for use with the substrate of the present invention are described in:

Pederson, et al., "Antigenic Relationship of the Feline Infectious Peritonitis Virus to Coronaviruses of Other Species", *Archives of Virology* 58, 45–53 (1978)

Pederson, "Serologic Studies of Naturally Occurring Feline Infectious Peritonitis" *Am. Journal of Vet. Res.,* 37 No. 12, 1449–1453 (197 )

Horzinek, et al., "Virology and Pathogenesis of Feline Infectious Peritonitis", *Archives of Virology* 59 1–15 (1979)

Assays for feline leukemia suitable for use with the substrate of the present invention are described in:

Jarrett, et al., "A Comparison of Three Methods of Feline Leukemia Virus Diagnosis", *The Veterinary Record,* 325–328 (1982)

Hirsch, et al., "Comparison of ELISA and Immunofluorescence Assays for Detection of Feline Leukemia Virus Antigens in Blood of Cats", *Journal of the Amer. Animal Hospital Assoc.* 18 933–938 (1982).

Thus, for example, the preferred embodiment of the present invention wherein the P-27 antigen of the feline leukemia virus is bound to the substrate may be used to diagnose feline blood for the presence of Feline Leukemia Virus. Likewise, the embodiment wherein the TGE virions are bound to and within the substrate may be used to diagnose feline infectious peritonitis and preferred embodiment wherein the toxoplasma gondii antigen is bound may be used to assay feline blood for toxoplasmosis antibodies.

The protein-binding immuno-substrate may be prepared by blending an acrylic copolymer comprised of 50% resin and 50% water at pH about 8 to 9 (Ingredient A) with an emulsion of acrylic resin and water blended with a suspension of titanium doxide and zinc oxide (Ingredient B) and an emulsion of acrylic resin and water blended with a suspension of titanium dioxide and copper phthalocyanine (Ingredient C). Ingredient B may comprise, in addition, a flow-enhancer, tall ester resin, for example. Preferably, Ingredient B comprises about 3-5% of tall ester resin. The ingredients are preferably combined the ratio of A:B:C=2.5:2.5:1 and diluted prior to use in 5 parts of distilled water.

The acrylic copolymer may be derived from an acrylic emulsion source, such as methacrylic acid or polymethyl methacrylate or copolymers of combinations of these.

The substrate may be also derived from vinyl acetates and derivatives, or from butadiene-styrene and copolymers of these with other polymers. It may be epoxy polymer materials, vinyl chloride materials and copolymers of any and all of the above.

The resin in ingredients A,B and C is preferably in bead-like form with beads being of diameters between about 0.1 to 1.0 micron, most preferably about 0.2 microns. The oxides in ingredients B and C are particles chosen to be about the size of one-half the wavelength of light directed on the sample. For the fluoroassays of the present invention, for example, the particles are preferably about 0.2 microns. The phthalocyanine compounds randomly distributed in the polymer matrix are less than 0.1 micron and are preferably between 0.05 to 0.1 microns.

A preferred embodiment comprises FITC as the dye label and copper phthalocyanine as the scattering pigment particle. Optimum sizing of the particles is based upon Mie scattering theory and indicates that optimum scatter occurs when the particle diameter is approximately half the wavelength of light. Since, with FITC as the dye molecule, "blue" light of wavelengths 420 to 480 nanometers is directed at the film, it would be ideal to have particles of 0.2 to 0.3 microns diameter.

The acrylic polymeric beads and the titanium dioxide preferrably have diameter distributions which are maximum at about 0.2 microns. The copper phthalocyanine preferrably comprises particles somewhat smaller, but still represents an efficient scattering cross section.

In preferred embodiments of the invention, the substrate is immobilized on a solid support. The solid support preferably has an essentially flat surface upon which the substrate is deposited in at least one discrete area. Most preferably the solid support comprises in addition one or more test wells having substantially flat bottom surfaces and diverging side walls. The substrate is preferably immobilized on the flat bottom surfaces of the wells. The wells with substrate deposited thereon thus provide a contained area wherein assay of a fluid may proceed. When immobilized under controlled temperature and humidity conditions (e.g. 68° F. and 70% humidity), a colloidal film is formed of 40 to 50 microns thickness and is water permeable.

At controlled rates of drying (temperature and humidity not to fluctuate or be extreme and no exposure to drafts be tolerated); and, at the appropriate dilution with distilled water as indicated in the formulation, a liquid deposit of the emulsion about 75 microns in height is coalesced into a thick film of about 40 to 45 microns as shown in electron micrographs.

When dry, a typical film weight is 60 to 65 milligrams. After ten minutes exposure to aqueous solutions (for instance, after pre-soaks in water, or deposits of body fluids), the weight of the film increases to 115 milligrams, a 75% increase due to water content. Even after 1½ hours of subsequent drying at room temperature, a residual excess of 6 to 7% water content is present which disappears exponentially.

The immobilized substrate of the present invention may be used for immunoassay in conjunction with testing devices which measure the amount of light of a particular wavelength transmitted by the substrate and reactants absorbed thereon and therein. Co-pending U.S. patent application Ser. No. 362,696 filed Mar. 29, 1982 discloses one such testing device and is incorporated herein by reference. When used with this testing device and system, available from Daryl Laboratories under the TRACK XI trademark, a light having a wavelength substantially similar to the excitation mode of the fluorophor is directed at the substrate. The incident light is reflected, transmitted or absorbed in amounts proportional to the amount of reactants on and in the substrate. When the incident light is of a wavelength in the fluorescent label's excitation spectrum, the particulate material in the substrate, preferably a phthalocyanine pigment, copper phthalocyanine, for example, reflects this specific incident light and absorbs any non-fluorescent activating light. The sensitivity of the assay is thus greatly increased since the background level of unwanted reflected light is reduced and the signal to background ratio of reflected fluorescent light is enhanced.

The immobilized substrate also enhances the sensitivity of assays which involve other chromophoric groups, enzyme immunoassay (EIA), for example. In EIA, the incident light travels through a liquid medium to the immobilized substrate on which the immunoreaction takes place, whence it is reflected back through the liquid medium which is the enzyme reactant undergoing color change.

In a preferred embodiment of the present invention, the substrate may comprise in addition a first substance which is capable of reacting with one or more subsequent substances to form a fluorescent product. Thus, for example the substrate may have bound thereto or therein an antigen or antibody capable of reacting with its respective ligands which is tagged with an appropriate fluorophor. In this embodiment, the substrate is of use in assay of biological fluids which may contain antigens or antibody characteristic of a particular viral, parasitic or bacterial infection and thus is a useful diagnostic tool. Assays of great sensitivity may be performed with speed and reproducibility and are thus useful in the routine screening of large numbers of samples from animals suspected of infection. Other examples of substances which may be bound to the substrate of the present invention are peptides, hormones, drugs or enzyme substrates. These substances may be detected by direct assay with a reagent which may be tagged with a fluorophor or may be detected by indirect assays, as for example, the sandwich technique.

The following examples illustrate the use of the present invention in the immunoassay of fluids in the diagnosis of diseases. However, it is to be understood that the invention is not to be limited by these examples.

EXAMPLE 1

Feline Leukemia Assay

A. Antibody depletion assay

Substrate was immobilized on the bottom of test wells in a solid support furnished by Daryl Laboratories under the trademark COLLIMMUNE and prepared as described herein with reference to the substrate composition and the test tracks of U.S. patent application, Ser. No. 399,920 filed July 19, 1982 now U.S. Pat. No.

4,468,371. P-27 antigen, one of the core antigens of the feline leukemia virus, was harvested from growing cell line Fl-74 and deposited on a first test well.

In an auxiliary test well a sample containing P-27 antigen was incubated with anti-P-27 antibody developed in rabbits. After a 10-minute incubation, a portion of this mixture was transferred to the first test well to allow any free antibody not already bound to sample antigen to combine with the P-27 antigen in the substrate. After a 15-minute incubation and a brief wash, goat anti-rabbit immunoglobulin G (IgG) which was fluorescein isothiocyanate (FITC) labelled was added to the substrate. After a 10-minute incubation the substrate was washed and inserted into a Daryl TRACK XI device as described herein and measured for transmitted fluorescence light. Calibration samples for leukemia virus were normal cat sera containing known concentrations of the P-27 antigen.

Clinical trials on 104 previously frozen cat serum samples demonstrated a specificity of 85% and a sensitivity of 95% against a comparative ELISA subjective sandwich assay, the Leukassay F TM from Pitman Moore, Inc..

EXAMPLE 2

Fluoroimmuno Assay of Feline Infectious Peritonitis (FIP)

The Daryl TRACK XI System Assay for FIP antibodies is a standard "sandwich type" assay, however, each sample is tested on both an antigen coated well and a control coated well. The COLLIMMUNE substrate was the same as used in Example 1.

To alternate wells were applied control preparation and antigen preparation. Control preparation was supernatant obtained from cultured pig kidney (PK) cells diluted 1:3 with 0.1 M bicarbonate buffer, pH 9. Antigen preparation was TGE virions obtained from supernatant from cultured PK cells infected with TGE virus (Miller Strain). Feline infectious peritonitis antibodies strongly cross react with TGE virus.

Feline Blood Sample was applied to both control and antigen wells and incubated for 10 minutes. After a wash, rabbit anti-cat IgG with FITC label was then applied to the wells. After 10 minutes incubation and a final wash with water, the wells were observed for fluorescence in the TRACK XI Fluorescent Reader. In analyzing the results, the fluorescence of control is subtracted from the antigen well derived fluorescence of both calibrated samples and unknown samples, to give a net fluorescent reading. Calibrated samples are pooled sera of known FIP titer as determined by other techniques. Clinical trials on 124 samples of previously frozen cat serum samples showed specificity of 80% compared to the known kinetic enzyme linked assay (KELA). The TRACK XI assay showed 90% sensitivity compared to the KELA assay.

EXAMPLE 3

Fluoroimmunoassay of *Toxoplasma gondii*

*Toxoplasma gondii* may affect many different animals, but the cat serves as its natural reservoir. It is of serious clinical significance since transmission from household cat to a pregnent owner may lead to catastrophic birth defects in the fetus. Accordingly, both the pregnant woman and her cat should be tested periodically by serology during the term of her pregnancy.

To substrate as in Example 1 is added soluble antigens extracted from disrupted *Toxoplasma gondii* organisms. Substrate and antigen are immobilized in test wells. One drop of whole, undiluted serum or blood is placed in each well. The wells are incubated 10 minutes at room temperature to allow reaction between antibodies to T. gondii and the immobilized antigen. The wells are washed and then contacted with anti-feline antibodies labelled with fluorescein isothyisocyanate (FITC). After 10 minutes incubation the wells were washed and observed for fluorescence. Control samples of known titer were run simultaneously to establish a calibration curve.

EXAMPLE 4

The following assays were carried out using the general procedure, substrate and equipment of Examples 1-3. Feline IgG was done like the Example 3 but *no* antibody or antigen was pre-applied to the colloid substrate. Serum was placed in wells for 10 minutes. All serum proteins were absorbed. After washing, anti-feline IgG antibody with FITC label was applied. It reacted only with the bound IgG. After a 10-minute incubation, excess anti-feline IgG was washed away and fluorescence was read in the TRACK XI instrument. Calibrators provided quantitation in mg of IgG per 100 ml of blood.

Equine IgG assay was carried out in the same fashion as in the feline IgG assay but was calibrated for low levels to determine if a newborn foal was immunodeficient—not having taken the colostrum from the mare.

Canine Distemper antibody, Canine Parvovirus antibody, and Canine antibody to Brucella were all sandwich techniques carried out similar to Example 3 and directed against the appropriate antigens. All employed two 10-minute incubations and two brief washes. None required the use of control wells as did the FIP test of Example 2. For a Rheumatoid Factors test in dogs, the antigen was "altered" rabbit IgG to which, in some dogs, IgM antibodies are directed. An anti-dog IgM FITC labelled antibody was used in the same fashion as Examples 1-3. For a canine antinuclear antibody test, double and single stranded DNA plus ribonuclear protein were combined as antigen. The test was conducted as in Examples 1-3.

Immunologic tests,viral, involing detection of antigens or antibodies to antigens of viral, bacterial nad parasitic origin, that can be carried out according to the present invention include, *inter alia*, the following:

Small companion Animals:
F. Leukemia Virus
F. Infectious Peritonitis
F. Toxoplasmosis
F. Infectious Anemia
C. Heartworm
C. Brucellosis
C. Parvovirus
C. Anti-Nuclear Antibodies
C. Rheumatoid Factors
C. Distemper
Equine:
E. Infectious Anemia
E. Pregnancy
E. Strangles
E. Pneumonitis
E. Metritis
E. Influenza
Laboratory:

Viral panels for Mice and Rats
Food and Fiber:
Bovine Brucellosis
Trichinella
Gastro-enteritis of swine
Blue Tongue Virus Disease
Avian:
Newcastle's Disease Virus
Psittacosis
Leukosis In addition, quantitation of IgG, IgA, IgM and IgE, serum protein components of the complement systems and other serum proteins like C reactive proteins are possible.

What is claimed is:

1. Substrate for fluoroimmunoassay comprising:
   (1) swellable, rehydratable protein binding matrix forming a three-dimensional polymeric matrix;
   (2) first particulate light scattering centers distributed in the polymeric matrix which scatter visible light; and
   (3) second particulate light scattering centers distributed in the polymeric matrix which reflect fluorescent excitation light of a particular wavelength or frequency and absorb all other light.

2. Substrate of claim 1 wherein said polymeric protein binding material is an acrylic copolymer.

3. Substrate of claim 2 wherein said acrylic copolymer is comprised of methacrylic acid and polymethyl methacrylate.

4. Substrate of claim 1 wherein said first particulate light scattering centers are oxides of titanium and zinc, separately or in combination.

5. Substrate of claim 1 wherein said second light scattering center is a phthalocyanin compound.

6. Substrate of claim 1 immobilized on a solid support.

7. The substrate of claim 6 wherein said solid support comprises an essentially flat surface.

8. A substrate as in claim 7, wherein said substrte is immobilized on the bottom of a solid support which comprises one or more test wells having essentially flat bottom surfaces and diverging side walls.

9. Substrate of claim 1 having bound therein and thereto a first substance capable of reacting with one or more subsequent substances to form a fluorescent product.

10. Substrate of claim 9 wherein said first substance is an antigen or antibody.

11. Substrate of claim 10 wherein said antigen is TGE virions, the P-27 antigen of feline leukemia virus, *Toxoplasma gondii*, canine distemper virus, canine Parvovirus, canine Brucella organisms, Brucella abortus organisms, heartworm or Trichinella.

12. An immunoassay method for determining or detecting the presence or absence of an immunogen comprising:
    (1) contacting a fluid suspected of containing said immunogen to a substrate useful for fluoroimmunoassays, said substrate comprising:
       (a) swellable, rehydratable protein binding material forming a three dimensional polymeric matrix;
       (b) first particulate light scattering centers distributed in the polymeric matrix which scatter all visible wavelengths of light; and
       (c) second particulate light scattering centers distributed in the polymeric matrix which scatter only fluorescent excitation light of a particular wavelength or frequency and absorb all other light;
    (2) incubating the fluid and substrate under conditions favoring binding of immunogen to said substrate;
    (3) adding a sample of a material known to specifically bind to the immunogen, said material having bound thereto a fluorescing dye molecule;
    (4) incubating the substrate with immunogen bound thereto with said sample under conditions favoring binding of said material to the immunogen;
    (5) removing non-bound material, and;
    (6) observing scattering of light from the fluorescing dye molecule or lack thereof, the presence of said scattering indicating presence of the immunogen, and lack of said scattering indicating absence of the immunogen:

13. Immunoassay of claim 12, wherein said material has an enzyme linked thereto.

14. A method as in claim 12, wherein said method is used to diagnose mammalian diseases caused by bacterial, viral, parasitic, or fungal infection.

15. A method as in claim 14, wherein said method is used to diagnose feline leukemia virus, Toxoplasmosis in humans and other mammals, feline IgG, canine IgG, canine distemper, canine Parvovirus, or canine Brucella.

* * * * *